(12) United States Patent
Capstick et al.

(10) Patent No.: US 9,763,734 B2
(45) Date of Patent: Sep. 19, 2017

(54) ELECTROMAGNETIC FIELD APPLICATOR ARRAY WITH INTEGRAL SENSORS FOR IMPLICIT CORRECTION OF MUTUAL COUPLING AND MISMATCH

(75) Inventors: Myles Capstick, Zürich (CH); Niels Kuster, Zürich (CH); Sven Kuehn, Zürich (CH); Esra Neufeld, Zürich (CH)

(73) Assignee: Foundation for Research on Information Technologies in Society, Zurich (CH)

( * ) Notice: Subject to any disclaimer, the term of this patent is extended or adjusted under 35 U.S.C. 154(b) by 642 days.

(21) Appl. No.: 13/261,600

(22) PCT Filed: Sep. 6, 2011

(86) PCT No.: PCT/EP2011/065402
§ 371 (c)(1),
(2), (4) Date: Feb. 21, 2013

(87) PCT Pub. No.: WO2012/032053
PCT Pub. Date: Mar. 15, 2012

(65) Prior Publication Data
US 2013/0237742 A1  Sep. 12, 2013

(30) Foreign Application Priority Data

Sep. 6, 2010  (CH) ...................................... 1439/10

(51) Int. Cl.
*A61B 18/04* (2006.01)
*A61B 18/18* (2006.01)
(Continued)

(52) U.S. Cl.
CPC .......... *A61B 18/18* (2013.01); *A61B 18/1815* (2013.01); *A61B 18/12* (2013.01);
(Continued)

(58) Field of Classification Search
CPC ..... A61B 18/12; A61B 18/18; A61B 18/1815; A61B 2018/0016; A61B 2018/00827;
(Continued)

(56) References Cited

U.S. PATENT DOCUMENTS 4,672,980 A  6/1987  Turner
4,885,589 A  12/1989  Edward et al.
(Continued)

FOREIGN PATENT DOCUMENTS

WO   WO 88/03823   6/1988
WO   WO 93/00132   1/1993
(Continued)

OTHER PUBLICATIONS

Calibration Techniques for Digital Phased Arrays, Fulton C; Chappell, W.; Microwaves, Communications, Antennas and Electronics Systems, 2009. COMCAS 2009. IEEE International Conference on Communications, Antennas and Electronic Systems. Publication Year: 2009, pp. 1 -10.

*Primary Examiner* — Jaymi Della
(74) *Attorney, Agent, or Firm* — George Pappas (57) ABSTRACT

A system for producing specific field distributions in a defined volume or region comprises: an array of electromagnetic field generating elements each with an integrated sensor for measuring the phase and amplitude of the current flowing in a metallic element or the field in a slot based element; a measurement device to enable measurement of both phase and amplitude of the electrical signals from the sensors with sufficient dynamic range for quantification of the signal; a multi channel radio frequency power source with individually controllable amplitude and phase to excite each of the electromagnetic field generating elements, and a feedback controller enabling controlled adjustment of the amplitude and phase of the radio frequency power source based on the signals from the sensors. The superposition of (Continued)

the fields produced by each electromagnetic field generating element produces a desired electromagnetic field distribution in the defined volume or region.

15 Claims, 6 Drawing Sheets (51) Int. Cl.
- A61B 18/12 (2006.01)
- A61B 18/00 (2006.01)
- A61N 1/40 (2006.01)

(52) U.S. Cl.
CPC ......... *A61B 2018/0016* (2013.01); *A61B 2018/00827* (2013.01); *A61B 2018/00869* (2013.01); *A61B 2018/00892* (2013.01); *A61N 1/403* (2013.01)

(58) Field of Classification Search
CPC ........... A61B 2018/00869; A61B 2018/00892; A61N 1/403; A61N 2005/027; A61N 5/027; A61N 5/025; A61N 5/022; A61N 5/02

See application file for complete search history.

(56) References Cited

U.S. PATENT DOCUMENTS

| | | |
|---|---|---|
| 5,251,645 A | 10/1993 | Fenn |
| 5,441,532 A | 8/1995 | Fenn |
| 5,867,123 A | 2/1999 | Geyh et al. |
| 6,208,903 B1* | 3/2001 | Richards et al. ............. 607/101 |
| 6,904,323 B2* | 6/2005 | Samulski ...................... 607/101 |
| 2004/0061644 A1 | 4/2004 | Lier et al. |
| 2006/0265034 A1* | 11/2006 | Aknine et al. ................ 607/101 |
| 2008/0297402 A1 | 12/2008 | Wooldridge |
| 2014/0012063 A1* | 1/2014 | Turner .................... A61N 2/02 600/10 |

FOREIGN PATENT DOCUMENTS

| | | |
|---|---|---|
| WO | WO 96/40369 | 12/1996 |
| WO | WO 2004/103456 A2 | 12/2004 |
| WO | WO 2007/146175 A2 | 12/2007 |
| WO | WO 2008/068485 A2 | 6/2008 |

* cited by examiner

ELECTROMAGNETIC FIELD APPLICATOR ARRAY WITH INTEGRAL SENSORS FOR IMPLICIT CORRECTION OF MUTUAL COUPLING AND MISMATCH

This application claims priority from PCT Application No. PCT/EP2011/065402 filed Sep. 6, 2011 which claims priority from Switzerland Application No. CH 1439/10 filed on Sep. 6, 2010, which applications are incorporated herein by reference.

BACKGROUND OF THE INVENTION

This invention relates to systems for creating specific electromagnetic field conditions within specific regions in space, or for focussing electromagnetic energy into dielectric objects with enhanced control.

The ability to create specific electromagnetic field conditions is a core requirement in many medical applications from imaging to therapies. The present invention has applications in both these disciplines, as well as in phased array technology employed for communications and sensing applications.

One application of this invention is the generation of specific field conditions at certain locations in the human body for the purpose of hyperthermia.

The National Cancer Institute of the US National Institutes of Health defines Hyperthermia (also called thermal therapy or thermotherapy) as a type of cancer treatment in which body tissue is exposed to high temperatures (up to 45° C.). Research has shown that high temperatures can damage and kill cancer cells, usually with minimal injury to normal tissues. By killing cancer cells and damaging proteins and structures within cells, hyperthermia may shrink tumors.

This invention is concerned with local hyperthermia in which heat is applied to a small region, such as a tumor. It is possible to use various techniques to deliver energy to heat the tumor. In the context of this invention, either microwave or radio frequencies may be employed to apply the heat. Depending on the tumor location, there are several approaches to local hyperthermia. In the present case, an external approach is employed to treat tumors. The energy is applied by means of an applicator. The applicator is made up of a number of elements that are positioned around or near the appropriate region, and energy is focused on the tumor to raise its temperature using phased array techniques.

Hyperthermia is often applied in combination with other therapies such as radiation therapy and/or chemotherapy. Hyperthermia has been performed as part of the treatment of many types of cancer, including sarcoma, melanoma, and cancers of the head and neck, brain, lung, esophagus, breast, bladder, rectum, liver, appendix, cervix, and peritoneal lining (mesothelioma).

A phased array antenna is an antenna made up from a number of small(er) radiating elements, each with its own feed point. Phased array antennas are electrically steerable, which means the physical antenna can be stationary yet the antenna pattern can be manipulated by adjusting the amplitude weighting and phases of each element such that it is focused towards a particular region or such that it enables location of objects in space. Phased arrays can also be utilized to generate specific field conditions at certain locations in space or to focus radio frequency (RF) energy into dielectric objects in order to elevate the temperature of a target region inside the dielectric object or patient or induce fields and currents in a patient to excite atoms, nerves or other cellular mechanisms.

A phased array can be used for hyperthermia by focusing RF energy into the patient such that the temperature is elevated. When a phased array is used for this purpose, it is termed an applicator as it applies energy to the patient. The phased array or applicator elements are fed by a multi-channel RF or microwave power source where the phase and amplitude signals are agile such that the RF or microwave energy can be focused in a target region or tumor. The number of array elements and placement of these elements with respect to the target region define the quality of the focus that can be achieved.

The exemplar of RF hyperthermia will be used to illustrate the benefits of the invention. Although many systems have been proposed and used in the past for hyperthermia treatment of tumors, either alone or in conjunction with other therapies, the consistency and quality of the treatment has generally been lacking. Of utmost importance in local hyperthermia is the ability to apply or focus the energy from the applicator into the target region, tissue or tumor. To achieve satisfactory treatment outcomes, the whole target region should be heated sufficiently. To ensure this, a good electromagnetic applicator and patient specific models are most preferably used to plan and optimize the treatment. This step of accurately predicting the deposition of energy (and/or temperature rises) and optimizing such for best tumor treatment has been lacking in hyperthermia systems and has contributed to poor outcomes. During the treatment itself, in which RF or microwave power is applied to the hyperthermia array with the excitation amplitudes and phases as determined from the treatment plan, it is essential from a quality assurance point of view that the electromagnetic fields generated by each element is monitored to determine that the correct planned treatment is actually being applied.

Common to all phased array antennas or hyperthermia applicators, is the requirement for a multichannel source which can generate powerful signals with accurately controllable amplitude and phase with which to feed the individual electromagnetic field generating elements. It is not important for this invention which method is used to generate these signals.

Multi-element or phased array applicators generally dispose the elements of the array around the patient with a water bolus filling the space between patient and array to provide surface cooling and lower reflections at the patient interface. U.S. Pat. Nos. 4,672,980, 5,251,645 and 5,441,532 all show typical phased array applicators. Each has the elements disposed in a circular array around the patient with the individual antenna elements (or pairs of elements in U.S. Pat. No. 4,672,980) excited by an RF power source with controlled amplitude and phase. None of these systems measure the actual applied signals or any power reflected which would reduce the effective radiated power. These factors therefore increase the uncertainty, In U.S. Pat. Nos. 5,251,645 and 5,441,532, field sensors are placed in and around the body of the patient to measure the overall applied field at those points and claims that using the values from these sensors the array excitation can be controlled such that the energy is focused into the target. U.S. Pat. No. 4,672,980 uses a different approach where temperature measurement catheters are inserted into the patient and the system controlled to maximize the temperature increase in the target region. The draw-back of both approaches is that the human body is highly inhomogeneous and there is no intuitive relationship between applied excitations of the array and the energy deposition pattern. In essence these approaches assume that knowing the field or temperature at a few points is a substitute for knowing the radiation from each array element.

In the literature, Paulides et al 2007 describe a typical state of the art system, where the magnitude and phase of the applied signals to each applicator element is measured along with the reflected power, such that the control values can be adjusted such that the applied signals in light of reflections are as desired. When used with proper treatment planning this system has the potential to perform satisfactorily.

However, the system relies on a computer simulation model fully defining the actual device and no means is available to fully account for changes in registration of the patient with respect to the applicator for the element impedance and mutual coupling element of the excitation.

In the broader context of phased arrays for other applications, U.S. Pat. No. 5,867,123 uses a technique of exciting single elements and observing the signals received by adjacent elements for built-in testing and failure analysis. Fulton and Chappell, 2009, review different calibration techniques for phased arrays and states arrays should be calibrated in an anechoic environment to determine the coupling matrix to enable compensation of the mutual coupling in the array. Additionally, it is noted that internal electronic hardware can be introduced for the monitoring of any changes from the initial calibrated coupling or transmit chain gains allowing correction to be applied. Lee et al, 1992/3, introduced a transmission (microstrip) line into the antenna panel to couple with each element so that transmit and receive functions of the electronics could be tested. The transmission line receives energy from all elements or injects energy into all elements of the array simultaneously.

SUMMARY OF THE INVENTION

Experience with radio frequency hyperthermia treatments and treatment planning and knowledge of the short-comings of systems of the nature discussed above, has led to important developments being made to the equipment and control systems. These developments greatly enhance certainty and consistency through assured field excitation. The present invention enhances consistency through assured field excitation from each antenna element of the array in the presence of mutual coupling, mismatch and reflections and hence uncertainty is reduced. Furthermore, the invention allows the coupling matrix to be determined more accurately than by the use of impedance or scattering matrix measurements, enabling a form of self-calibration which may be performed for each patient undergoing treatment. The key to achieving assured field excitation as determined by the treatment plan is the inclusion of sensors integrated into the antenna elements themselves which measure the phase and amplitude of current flowing in a metallic element or field in a slot-based element. These sensors, in the absence of mutual coupling or reflections, provide a measure proportional to the excitation. However, there is no requirement to consider mismatch or phase differences in connection leads, since it is the actual current (or field) in the antenna that is measured. With mutual coupling and reflections, the sensors measure the sum of all excitations, whatever their origin, and hence allows determination of the actual radiated field. Excitation of each element in turn and the measurement of the current (or field) in the excited antenna along with coupled excitation of all other antennas will allow the coupling matrix of the array to be directly determined.

U.S. Pat. No. 5,867,123 discussed above also excites each element in turn, but does not use this as a means to achieve self-calibration; even if it did, element mismatch would increase uncertainty. Lee et al, 1992/3 includes transmission lines introduced into the antenna panel, but lacks the ability to sense each antenna element individually, and does not disclose any motivation or ability to determine the antenna currents (or fields) due to either direct excitation or mutually coupled excitation. Hence, this system is used as a diagnostic tool rather than for control of field excitation.

The present invention comprises an array of electromagnetic field generating elements and integrates into each a sensor for measuring the phase and amplitude of the current flowing in a metallic element (antenna or coil) or field in a slot based element linked to a measurement device to enable measurement of both phase and amplitude of the electrical signals from each of the sensors, Furthermore, because signal picked up by each sensor is directly proportional to the phase and amplitude of the current or field in the associated electromagnetic field generating element where the current or field is the total current or field whose amplitude and phase is the sum of both the applied (from the radio frequency power source) and secondary excitations from mutual coupling and mismatch, hence the measured value represents the ideal excitation in the absence of mutual coupling and mismatch. This invention then uses embedded sensors in the antenna to add further functionality, for example, the direct excitation of each array element by a multichannel radio frequency or microwave power source, with individually controllable amplitude and phase, can be modified using a feedback controller such that the total excitation as measured by the embedded (current in a metallic or the field in a slot based antenna) sensor is the ideal array excitation without coupling or mismatch such that the superposition of the fields produced by each electromagnetic field generating element produces a specific electromagnetic field distribution in a defined volume or region. Implicitly correcting for the mutual coupling and mismatch without explicit knowledge of, and calculation based on, the mutual coupling and mismatch, termed the coupling matrix, such that changes in the coupling matrix due to presence of objects or changes thereof are inherently taken into account. Additionally, using sequential excitation of each element, the invention can directly determine the exact mutual coupling matrix of the array even in the presence of variations in source impedance and undefined cable lengths which can be useful in determining the initial excitation of the array of electromagnetic field generating elements such that feedback can more rapidly achieve the predefined ideal array excitation.

TECHNICAL DESCRIPTION WITH REFERENCE TO ACCOMPANYING DRAWINGS

The invention relates to a system made up of five integral parts, it is the novel features of some of these parts and the integration and use of them as a whole that provides the innovation. The first integral part are the electromagnetic field generating elements 6, FIG. 1, which are arranged pairwise on a platelet 1 into an array of arbitrary geometry, FIG. 2. The array of elements is connected to a radio frequency power source, FIG. 3, which has a frequency reference 7 and a number of independently phase and amplitude computer controllable channels each having a phase and amplitude controller 8, a driver 9, and a power amplifier 10 with an output 11. Integrated into each electromagnetic field generating element is a current (or field) sensing element which produces an electrical output proportional to the electromagnetic field generated, each electrical signal is measured by a measurement device that measures both amplitude and phase, FIG. 4. The measurement data is communicated via a measurement bus to a measurement controller. A control computer utilizes the measurement data to control the radio frequency power source in such a way that the electromagnetic fields generated are the required fields, the whole system and the interconnections are shown in FIG. 5.

Figure 5:
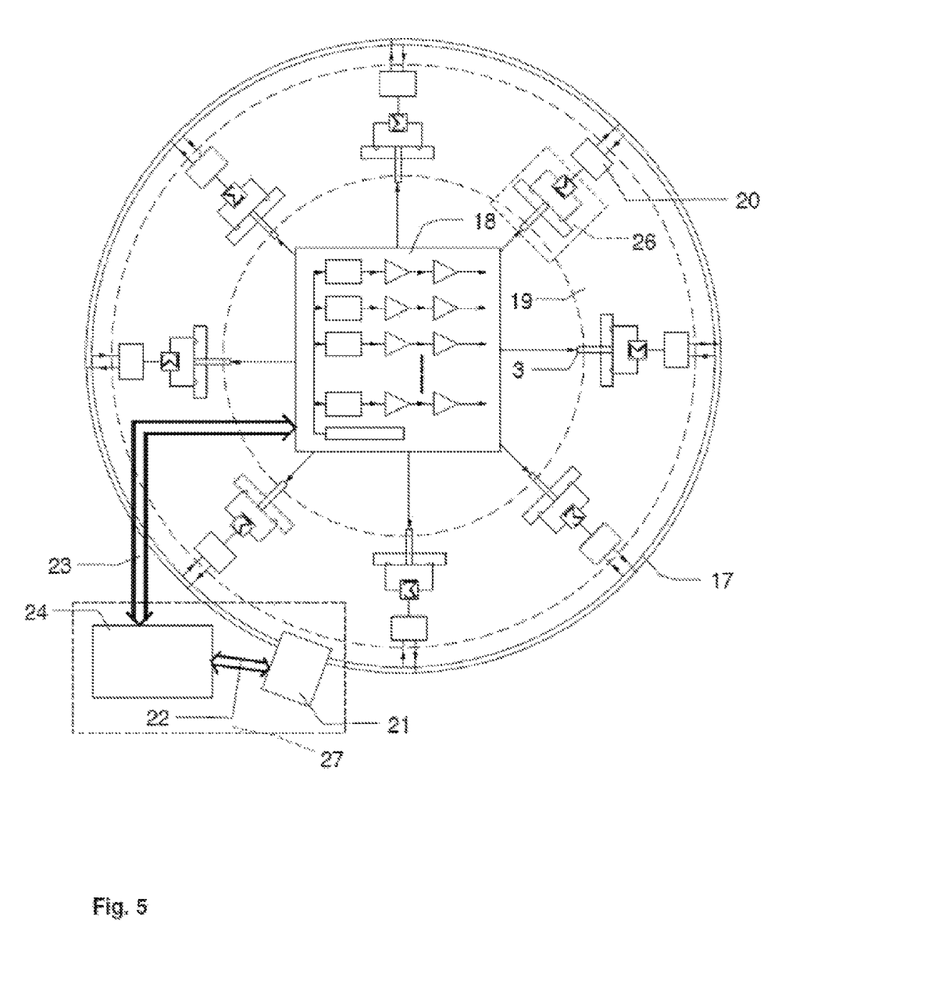
FIG. 5: is illustrative of a whole system with phase and amplitude controlled multi-channel transmitter and phase/amplitude detectors connected by a measurement bus to the measurement and computer controllers.

An illustrative application of the invention is a phased array 19 applicator system, FIG. 5, that can generate specific field conditions at certain locations in space or focus the RF energy into dielectric objects. The direct measurement of the currents or fields in metallic, slot or coil elements 26 allows direct quantification of the radiated or reactive fields generated by the electromagnetic field generating elements. More specifically, the invention provides the possibility to implicitly correct for the perturbations in the electromagnetic field generated due mutual coupling and mismatch in the applicator array 19 without explicitly measuring the coupling matrix and applying a correction to the excitations from the a radio frequency power source 18. The direct relationship between the current in a metallic element (or field in a slot based element) to the electrical output from the element sensor 4 to the radiated or reactive field can be determined by experimental or numerical means.

Figure 6:
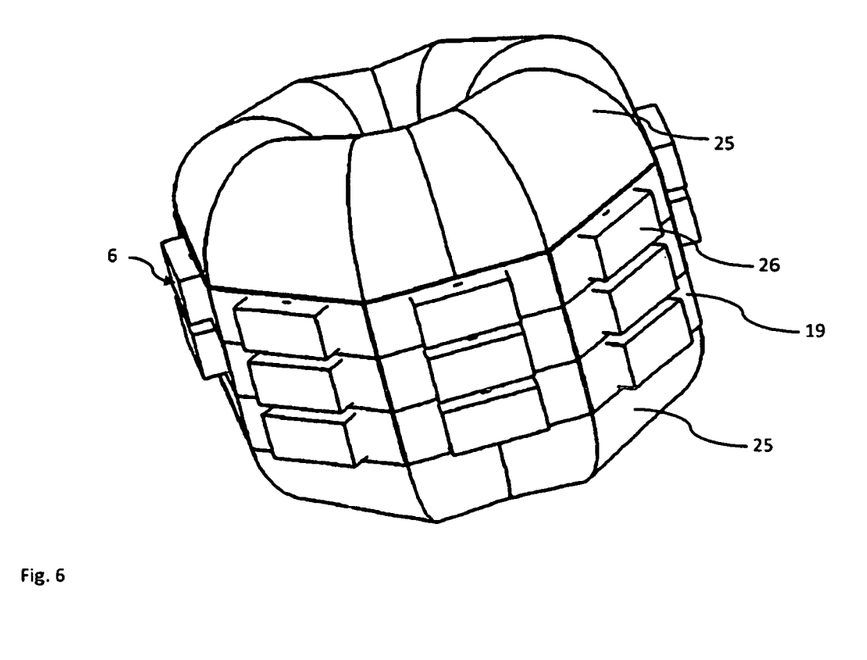
FIG. 6. is illustrative of an array for radio frequency hyperthermia in which a water bolus is shown for placement between the array elements and the patient to reduce reflection and facilitate surface cooling.

An objective of the invention is to provide an improved means of determining the actual radiated or reactive near field of each element 26, (corresponding to element 6 in FIG. 1), in an array 19 of electromagnetic field generating elements for radio frequency hyperthermia applications, (see FIGS. 2 and 6), where the immediate load due to patient, dielectric objects and other system components changes the coupling between and matching seen at the input ports 3 of the elements 26 or where the source impedance of the radio frequency power source output channels 11 are not well characterized.

Figure 4:
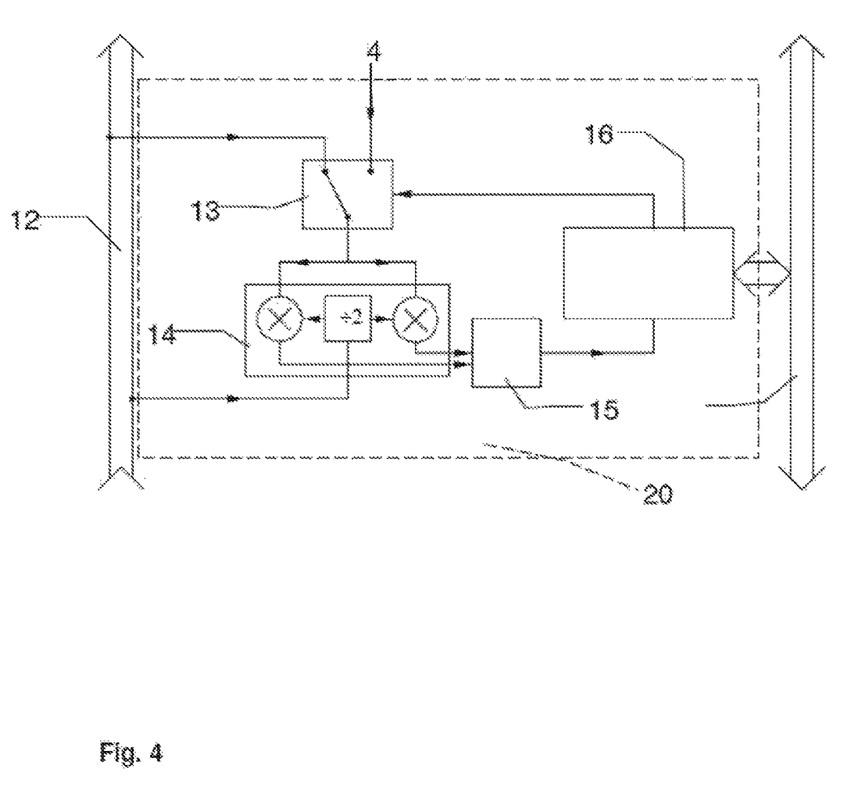

A further objective of the invention is to provide higher levels of confidence that the real array excitation from the multichannel radio frequency power source 18 is the planned excitation ensuring higher quality control of the field distribution generated by the array 19 of electromagnetic field generating elements. To enable this, the electromagnetic field generated is measured, FIG. 4, using a measurement device such as a vector volt meter or in-phase/quadrature demodulator of sufficient sensitivity. Additional circuitry may be added, as shown in FIG. 4, to allow self calibration of the amplitude and phase detectors facilitated by not only distributing the local oscillator via a bus but also a phase reference which can be switched to the input to allow calibration and/or phase ambiguity removal further reducing the uncertainty.

Additionally, the invention provides a new paradigm for the correction of array mutual coupling by implicitly measuring the generated electromagnetic field with the mutual coupling and mismatch accounted for. Hence the actual and planned excitations have a low deviation in particular in the presence of variations that could not be modeled during treatment planning.

Figure 2:
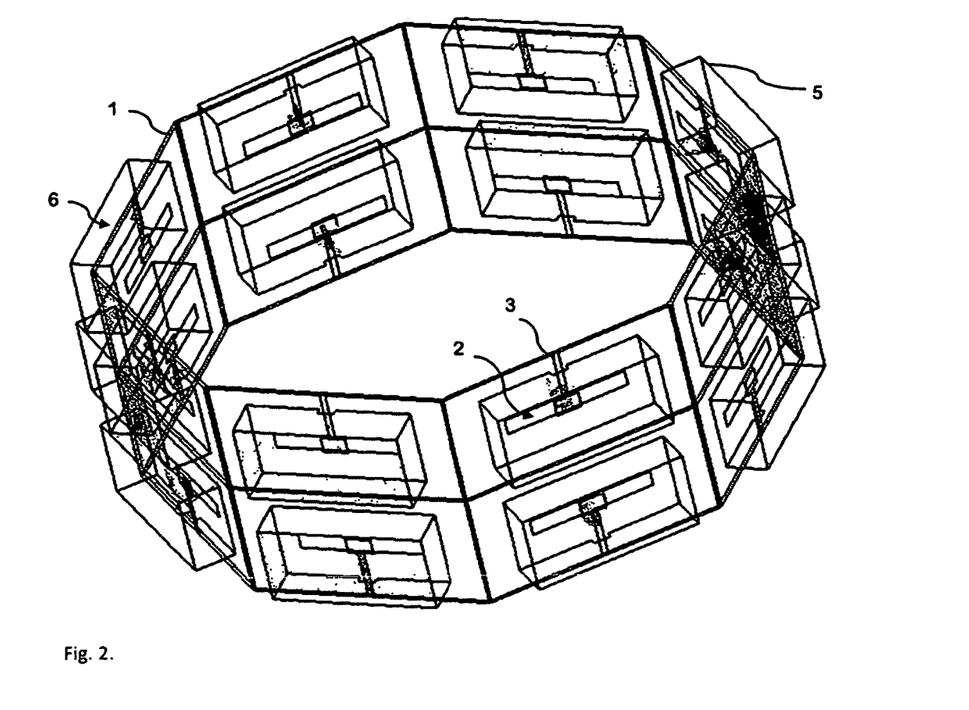
FIG. 2: is illustrative of a whole RF hyperthermia applicator phased array, detail of small sensor elements not included FIG. 3. Multi-channel radio frequency power source FIG. 4. Measurement Device, single channel

Furthermore, the invention does not limit the geometry or placement of the applicator array elements 26, FIG. 2, around or close to the target area and can be applied to any generic array of electromagnetic field generating elements 19. In particular there are no limits on the proximity of dielectric objects such as patients or other mutual coupling or element matching modifying attributes.

Figure 1:
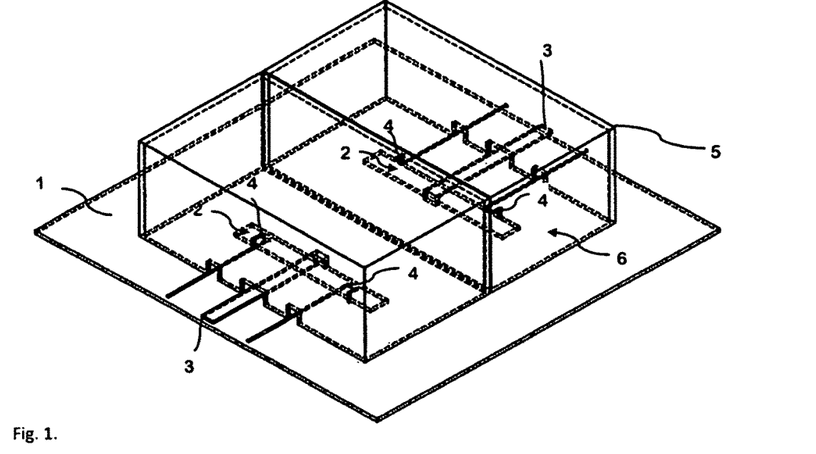
FIG. 1: is illustrative of two adjacent array elements (cavity backed slots) one showing the incorporation of one possible implementation of the present invention FIG. 1a Two adjacent array elements (cavity backed slots), with the cavity screening of one element cut away
Figure 1A:
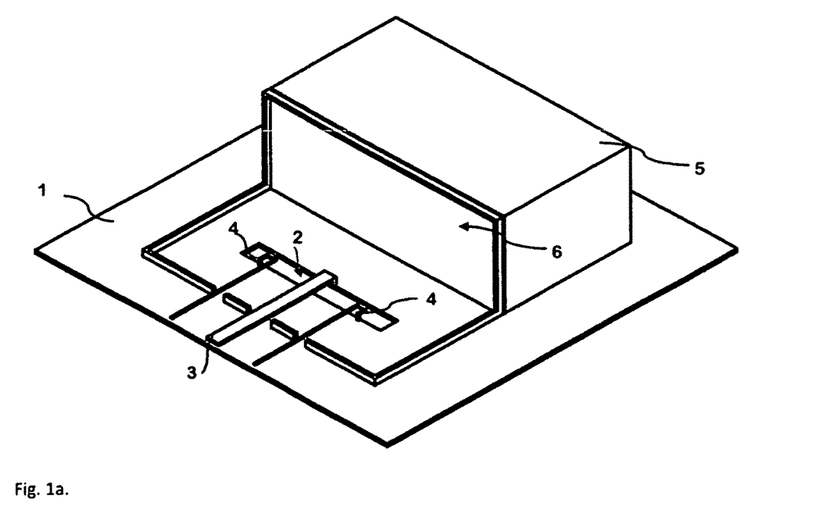

Though the integrated current or field sensors 4, FIG. 1, implicitly take into account mismatch and mutual coupling, the invention allows the coupling matrix (that describes the mismatch and mutual coupling) of the applicator array of electromagnetic field generating elements to be directly determined with greater accuracy than the standard technique of calculating the coupling matrix from the S-parameters and with the convenience of not having to disconnect the applicator array 19 from the radio frequency power source 18, FIG. 5, and connect it to a network analyzer. By excitation of each element 2 in turn using the radio frequency power source and measurement of the requisite currents (or fields) in all the elements 2 using the measurement device 18 the coupling matrix can be determined more accurately as the non-ideal output impedances of each amplifier 10 and connecting cable lengths between radio frequency power source output 11 and electromagnetic field generating element 3 are inherently accounted for.

The invention whilst providing this very important information on the radiated or reactive field from each element 26 also gives the ability to detect which output channel 11 from the multi channel radio frequency power source 18 has been connected to which electromagnetic field generating element 26 in the array 19 and hence remove the possibility of incorrect connection and the chance of a treatment that is completely in error.

With a measurement device 20 integrated with each element 26 it becomes possible to have an individual identity for each electromagnetic field generating element allowing individual calibrations for the element—measuring device combination to be assigned. Therefore, calibration data can be assigned to the correct element for means of quality control, ease of use and security. A calibration facility can therefore provide an accredited calibration that can be attributed to a given element. Enabling the whole array 19 to be modular with replaceable elements 26 and provide 'plug and play' capabilities.

DESCRIPTION OF THE PREFERRED EMBODIMENT

The preferred embodiment can be described in the context of an RF hyperthermia applicator system, FIG. 5. This hyperthermia applicator system consists of both hardware and a computer control systems and these systems allow enhanced use paradigms that illustrate the utility of the invention.

The Hyperthermia applicator system illustrated in FIG. 5 takes the form of a ring array applicator made up of electromagnetic field generating elements, FIG. 2, where the electromagnetic field generating elements, FIG. 1, are placed around the body in the vicinity of the region to be heated. It is not always the case that elements need to form an entire ring, but might be placed predominantly on one side of the patient. In this specific array however the E-field vector of all elements should be predominantly aligned in the same direction within the target region, but this is not a requirement in all applications of the system. The region between the applicator and the patient is filled by a water bolus, FIG. 6, of a defined shape which affords three things:
1. Miniaturization of the antenna elements due to the high dielectric constant.
2. Minimization of the discontinuity between antenna and patient as the dielectric properties of water and tissue are much more similar than air and tissue.
3. To provide cooling of the patient skin as high levels of specific energy absorption can occur on the body surface.

Cavity backed slot antennas, FIG. 1, are chosen as the electromagnetic field generating elements in our preferred embodiment as they provide: Low profile, good polarization purity, accurate dimensions through photolithographic printed circuit processing techniques, ease of manufacture, robust structure, relatively broadband response and hence tolerance to environment changes. With a slot antenna 2 embodiment then an appropriate method of sensing is through sensing of the field in the slot by means of sensors 4 configured as small coupling loops. The loops are sufficiently small such that the amount of coupled power is small compared to the total, which could be 100s of Watts, which is applied to the antenna port 3 and so that the field in the slot 2 remains unperturbed by the measurement. Each electromagnetic field generating element 6 is provided with a cavity screening 5

Figure 3:
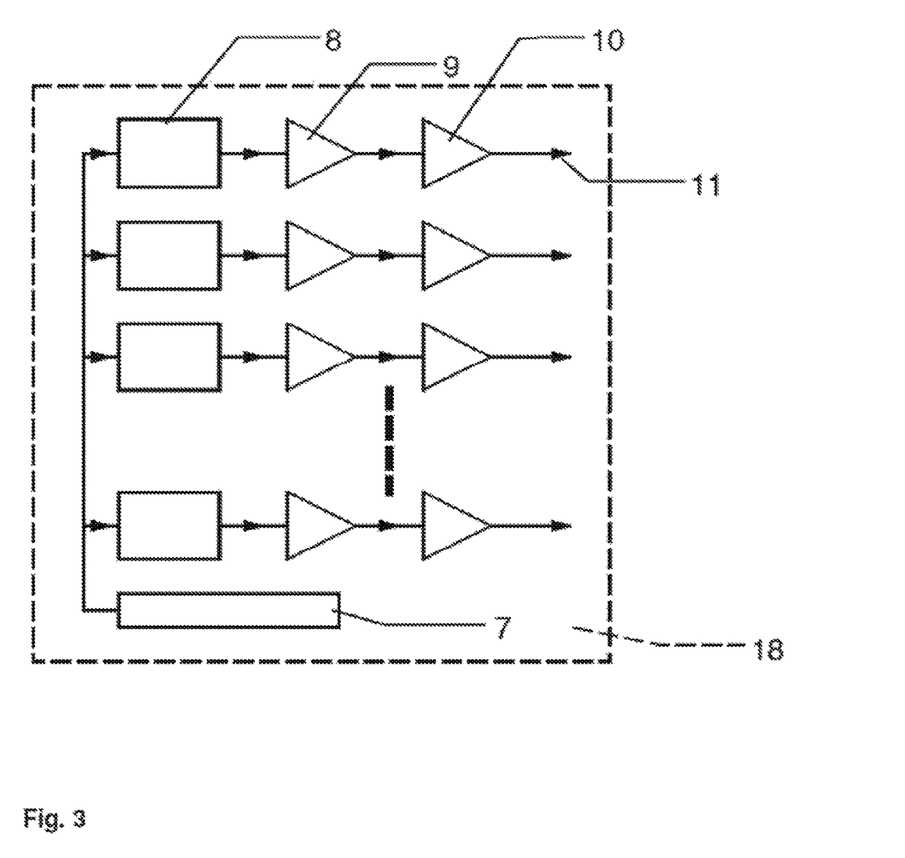

Each slot element in the applicator is fed from a phase and amplitude controllable radio frequency power source, FIG. 3. The fields in each applicator element slot due to its own excitation and fields coupled from other elements are sensed using sensors 4 and measured using measurement device 20 consisting of a phase/amplitude detectors, FIG. 4, and the values communicated to a measurement controller 21. In this case an in-phase/quadrature demodulator 14 in conjunction with a pair of analog to digital converters 15 is used to measure the in-phase and quadrature voltage levels. The digital signal is then converted into a magnitude and phase using the microprocessor 16 and communicated to the measurement controller 21 via a measurement bus 17.

A control system 27 comprising a control computer 24 connected with the measurement controller 21 via a control line 22 and connected with the radio frequency power source 18 via a feedback line 23 sets the amplitudes and phases of the phase and amplitude controllers 8 of the multi channel radio frequency power source 18 and measures by means of the measurement device 20 the resultant fields applied from each element 26 and affords feedback control to ensure the applied fields are the required fields.

A typical usage paradigm is that a validated numerical electromagnetic model of the applicator array 19 is used with a patient specific EM model derived from CT, M I or other image data within a treatment planning software. In the treatment planning software the target region or regions for treatment is defined and the optimum ideal excitation values (or non-ideal taking into account mutual coupling and mismatch based on the mutual coupling matrix for the model which may or may not closely correspond to the real coupling matrix due to the possible errors previously mentioned from which the ideal excitation can be calculated) are derived and the corresponding EM-field, SAR or temperature rise values across the whole of the target region or regions generated.

The target excitations are then transferred to the treatment control software and the patient placed in the applicator 19 at the position modeled in the treatment planning. The water bolus 25 is filled with deionized water.

The measurement devices 20 are put into calibration mode where the RF switch 13 in FIG. 4 is switched so that the calibration input phase reference signal from the bus 12 is measured by each measurement device to allow calibration of the phase of the device and also to remove the phase ambiguity of the /2 quadrature phase splitter in the in-phase/quadrature demodulator 14.

Each radio frequency power source output 11 channel of the multi channel radio frequency power source 18 is excited in turn to determine which applicator element 26 is connected to each output channel and to measure by means of sensors 4 the fields/currents induced in all the elements to generate the actual mutual coupling matrix for the array 19 at the time of treatment. In addition the phase and amplitude offset due to the connecting cables or transmit channel differences can be eliminated or calibrated out. Phase shifts due to variation in applicator element impedance from the ideal, for example due to patient proximity and hence change in the dielectric constant immediate environment, are also eliminated.

Treatment is commenced with radio frequency power 18 being applied to each element 26 based on the treatment planning, either based on ideal or corrected (using the coupling matrix) excitations, the actual excitation levels are determined using the field monitoring by means of sensors 4 and measurement device 20 and controlled by the feedback controller 27 to correct for any deviation from the desired excitation levels. Throughout the treatment the total output power from each channel 11 can be controlled by means of the phase and amplitude controller 8 and the correct relationship between amplitudes and phase can be monitored and controlled to the correct value by means of the measurement device 20. While the invention herein disclosed has been described by means of specific embodiments and applications thereof, numerous modifications and variations could be made thereto by those skilled in the art without departing from the scope of the invention set forth in the claims.

REFERENCES CITED

US Patents

U.S. Pat. No. 5,251,645
"Adaptive nulling hyperthermia array" Inventors: Fenn, Alan J. (Wayland, Mass.) Assignee: Massachusetts Institute of Technology (Cambridge, Mass.).
U.S. Pat. No. 4,672,980
"System and method for creating hyperthermia in tissue" Inventors: Turner, Paul F. Assignee: BSD Medical Corporation (Salt Lake City, Utah)
U.S. Pat. No. 5,441,532 and WIPO Patent Application WO/1993/000132 "ADAPTIVE FOCUSING AND NULLING HYPERTHERMIA ANNULAR AND MONOPOLE PHASED ARRAY APPLICATORS", Inventors: Fenn, Alan J. (Wayland, Mass.) Assignee: Massachusetts Institute of Technology (Cambridge, Mass.).

OTHER LITERATURE

Calibration techniques for digital phased arrays, Fulton, C; Chappell, W.; Microwaves, Communications, Antennas and Electronics Systems, 2009. COMCAS 2009. IEEE International Conference on Communications, Antennas and Electronic Systems. Publication Year 2009, Page(s): 1-10

A Built-in Performance-Monitoring/Fault Isolation and Correction (PM/FIC) System for Active Phased-Array Antennas, Kuan-Min Lee, uey-Shi Chu, and Sien-Chang Liu, IEEE TRANSACTIONS ON ANTENNAS AND PROPAGATION, VOL. 41, NO. 11, NOVEMBER 1993

K. M. Lee, R. S. Chu, and S. C. Liu, "A performance monitoring/fault isolation and correction system of a phased array antenna using transmission-line signal injection with phase toggling method," IEEE AP-S 1992 Symposium Digest (Chicago, Ill.), Jul. 18-25, 1992, vol. 1, pp. 429-432.

The invention claimed is:

1. A system for producing a predetermined electromagnetic field distribution in a defined volume or region, comprising a multi-channel radio frequency or microwave power source connected to electromagnetic field generating elements forming an array, the multi-channel radio frequency or microwave power source having a plurality of source channels, and a feedback controller for controlling the multi-channel radio frequency or microwave power source to achieve a desired electromagnetic field produced by each of the electromagnetic field generating elements, the desired electromagnetic field produced by each of the electromagnetic field generating elements being such that electromagnetic fields to superposition of the desired electromagnetic field produced by each of the electromagnetic field generating elements produces said predetermined electromagnetic field distribution in said defined volume or region, a feedback to the feedback controller being an amplitude and a phase of the desired electromagnetic field produced by each of the electromagnetic field generating elements, the system characterized in that current, electric field, magnetic field or electromagnetic field sensors are integrated into each of the electromagnetic field generating elements for sensing directly an element excitation and hence indirectly the amplitude and the phase of the desired electromagnetic field produced by each of the electromagnetic field generating elements, each one of said current, electric field, magnetic field or electromagnetic field sensors being interconnected in a 1:1 relationship with an associated measurement device for determining an amplitude and a phase of a signal from the associated current, electric field, magnetic field or electromagnetic field sensor and hence the desired electromagnetic field produced by each of the electromagnetic field generating elements.

2. The system according to claim 1 in which the electromagnetic field generating elements are coils or antennas, said antennas being based on conductor or slot elements.

3. The system according to claim 2 in which the associated measurement device is an In-phase/Quadrature (IQ) demodulator or vector voltmeter.

4. The system according to claim 1, in which the multi-channel radio frequency or microwave power source is provided with a control system for individually controlling amplitudes and phases of the radio frequency or microwave power source to produce individually controlled radio frequency or microwave outputs.

5. The system according to claim 4 in which the associated measurement device is an In-phase/Quadrature (IQ) demodulator or vector voltmeter.

6. The system according to claim 1, in which each one of said current, electric field, magnetic field or electromagnetic field sensors is configured to provide a direct indication of the amplitude and phase of the desired electromagnetic field produced by each of the electromagnetic field generating elements including mutual coupling between the electromagnetic field generating elements.

7. The system according to claim 6 in which the associated measurement device is an In-phase/Quadrature (IQ) demodulator or vector voltmeter.

8. The system according to claim 1 in which the associated measurement device is an In-phase/Quadrature (IQ) demodulator or vector voltmeter.

9. The system according to claim 1, in which each of the A electromagnetic field generating elements is integrated with a channel of the associated measurement device to form a module such that each module may be provided with an individual identity or serial number such that calibration data can be seamlessly assigned to each of the electromagnetic field generating elements, said modules are capable of being exchanged to enable rapid repair or servicing, and whereby the individual identity or serial number provides plug and play capability with automatic detection of different hardware and assignment of the calibration data.

10. The system according to claim 1, in which the feedback controller is configured to enable adjustment of an amplitude and a phase of each of the plurality of source channels of the multi-channel radio frequency or microwave power source.

11. The system according to claim 10, configured to be capable of implicitly correcting for a mutual coupling between and mismatch of the electromagnetic field generating elements.

12. The system according to claim 11, configured to be capable of describing the mutual coupling between and mismatch of the electromagnetic field generating elements in terms of a coupling matrix, the coupling matrix being determinable by exciting each electromagnetic field generating element in turn by a single source channel of the multi-channel radio frequency or microwave power source and using the element excitations sensed by all of the current, electric field, magnetic field or electromagnetic field sensors.

13. The system according to claim 12, in which the multi-channel radio frequency or microwave power source is provided with control means for individually controlling amplitudes and phases of the radio frequency or microwave power source to produce individually controlled radio frequency or microwave outputs, the system being configured to be capable of using the coupling matrix to calculate initial amplitudes and phases of the radio frequency or microwave outputs of the multi-channel radio frequency or microwave power source followed by using the element excitations measured by all of the current, electric field, magnetic field or electromagnetic field sensors and the feedback controller to fine tune the system to provide the desired electromagnetic fields produced by each of the electromagnetic field generating elements.

14. The system according to claim 1, adapted to focus radio frequency or microwave energy into one or more dielectric objects or one or multiple regions of said one or more dielectric objects, in order to excite atoms, molecules or cellular structures or to elevate temperature within said one or more objects or said one or multiple regions within the one or more dielectric objects.

15. The system according to claim 1 in which each source channel of the plurality of source channels of the multi-channel radio frequency or microwave power source is connectable in any order to each one of the electromagnetic field generating elements, the system being configured to use the current, electric field, magnetic field or electromagnetic field sensors to determine which source channel of the multi-channel radio frequency or microwave power source is connected to which of the electromagnetic field generating elements.

* * * * *

UNITED STATES PATENT AND TRADEMARK OFFICE
CERTIFICATE OF CORRECTION

| | |
|---|---|
| PATENT NO. | : 9,763,734 B2 |
| APPLICATION NO. | : 13/261600 |
| DATED | : September 19, 2017 |
| INVENTOR(S) | : Myles Capstick et al. |

It is certified that error appears in the above-identified patent and that said Letters Patent is hereby corrected as shown below:

Claim 1, Lines 36-37: delete "electromagnetic fields to"

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*